United States Patent
Ohara et al.

(10) Patent No.: US 6,936,724 B2
(45) Date of Patent: Aug. 30, 2005

(54) PROCESS FOR PRODUCING EPSILON-CAPROLACTONE

(75) Inventors: Eiji Ohara, Otake (JP); Ken-ichiro Kawazumi, Himeji (JP)

(73) Assignee: Daicel Chemical Industries, LTD, Osaka (JP)

( * ) Notice: Subject to any disclaimer, the term of this patent is extended or adjusted under 35 U.S.C. 154(b) by 0 days.

(21) Appl. No.: 10/688,926

(22) Filed: Oct. 21, 2003

(65) Prior Publication Data

US 2004/0087804 A1 May 6, 2004

(30) Foreign Application Priority Data

Oct. 22, 2002 (JP) ........................................ 2002-306710

(51) Int. Cl.$^7$ ............................................. C07D 313/04
(52) U.S. Cl. ......................... 549/272; 203/77; 203/81; 203/82; 203/86
(58) Field of Search .................... 549/272, 78; 203/77, 203/81, 82, 86

(56) References Cited

U.S. PATENT DOCUMENTS 4,341,709 A 7/1982 Hofen et al.

FOREIGN PATENT DOCUMENTS

| EP | 0 972 771 A1 | 1/2000 |
| JP | 53-34789 | 3/1978 |
| JP | 2002-179667 A | 6/2002 |

OTHER PUBLICATIONS

Perry, Chemical Engineers' Handbook, 5$^{th}$. Ed., McGraw–Hill, New York, p. Chapter 13, p.48 and 49 (1973).*

* cited by examiner

*Primary Examiner*—Bernard Dentz
(74) *Attorney, Agent, or Firm*—Birch, Stewart, Kolasch & Birch, LLP

(57) ABSTRACT

A process produces ε-caprolactone by the oxidation of cyclohexanone by feeding a crude reaction mixture to a first distillation column; distilling off a first distillate containing low boiling components including unreacted cyclohexanone from the top of the first distillation column; recovering a first side-cut fraction containing unreacted cyclohexanone in a higher concentration than in the first distillate from an intermediate tray; recovering a first bottom liquid containing high boiling components including ε-caprolactone from the bottom; introducing the first side-cut fraction to a second distillation column; recovering a second bottom liquid containing unreacted cyclohexanone from the bottom of the second distillation column; recycling the second bottom liquid into the raw material cyclohexanone; introducing the first bottom liquid to a third distillation column to thereby yield a third distillate containing ε-caprolactone from the third distillation column.

10 Claims, 2 Drawing Sheets

PROCESS FOR PRODUCING EPSILON-CAPROLACTONE

This Nonprovisional application claims priority under 35 U.S.C. §119(a) on patent application Ser. No(s). 2002-306710 filed in Japan on Oct. 22, 2002, the entire contents of which are hereby incorporated by reference.

BACKGROUND OF THE INVENTION

1. Field of the Invention

The present invention relates to a process for producing ε-caprolactone by the oxidation of cyclohexanone.

2. Description of the Related Art

ε-Caprolactone is widely used as a raw material for polyester polyols for the production of polyurethanes, and for other polymers as molding materials. ε-Caprolactone is typically produced by the oxidation of cyclohexanone. The oxidation of cyclohexanone is performed, for example, by a co-oxidation process in which cyclohexanone is oxidized with air in the coexistence of acetaldehyde or an oxidation process in which an organic peracid such as peracetic acid is used as an oxidizing agent.

In the production of ε-caprolactone by the oxidation of cyclohexanone, the resulting crude reaction mixture generally comprises unreacted raw material cyclohexanone, in addition to the target ε-caprolactone. In the oxidation using an oxidizing agent such as a peracid, the crude reaction mixture further comprises, for example, an unreacted oxidizing agent, by-products derived from the oxidizing agent (e.g., an acid derived from the peracid serving as the oxidizing agent), a solvent for the oxidizing agent, by-products derived from cyclohexanone (e.g., adipic acid), and a polymerized product of ε-caprolactone, in addition to the above components. The crude reaction mixture comprising multiple components is separated and purified by distillation to yield ε-caprolactone as a product and to recover and recycle unreacted cyclohexanone.

Demands have been made to increase the yield of ε-caprolactone by increasing the conversion from cyclohexanone as high as possible and to increase the productivity by reducing the amount of recovered and recycled cyclohexanone in the production of ε-caprolactone. As a possible solution to this, a process has been proposed in which the reaction is performed under severe conditions such as an increased amount of the oxidizing agent or an increased reaction temperature. However, this process also facilitates side reactions and thereby increases the by-products derived from cyclohexanone and by-products such as a polymerized product of ε-caprolactone. The reaction mixture containing these components should be heated in a distillation column for separation and purification, but the by-products further react with ε-caprolactone to yield more complicated by-products. Thus, the final yield of ε-caprolactone decreases, failing to achieve the initial object.

In contrast, a process in which steps relating to separation of ε-caprolactone and recovery of cyclohexanone are improved without changing reaction conditions has been proposed. For example, Japanese Unexamined Patent Application Publication (JP-A) No. 2002-179667 (p. 3–5 and FIG. 1) describes a process, in which a crude reaction mixture is fed to a first distillation column, a distillate containing cyclohexanone and a bottom liquid containing ε-caprolactone are separated, recovered and are then fed to second and third distillation columns for purification, respectively. However, according to this process, the distillate recovered from the first distillation column comprises cyclohexanone in a low concentration, and the second distillation column for recovering cyclohexanone must treat a large amount of the distillate. The size and treating capability of the second distillation column therefore must be increased, inviting increased energy for operation. Thus, the process is economically unadvantageous.

SUMMARY OF THE INVENTION

Accordingly, an object of the present invention is to provide an economically advantageous process for producing ε-caprolactone which can efficiently separate unreacted cyclohexanone from a crude reaction mixture and can efficiently yield high-quality ε-caprolactone.

After intensive investigations to achieve the above object, the present inventors have found that unreacted cyclohexanone can be efficiently separated and purified in a second distillation column by recovering a side-cut fraction containing unreacted cyclohexanone in a high concentration from a first distillation column, and that ε-caprolactone can be produced in a high yield by recycling the unreacted cyclohexanone.

Specifically, the present invention provides, in an aspect, a process for producing ε-caprolactone by the oxidation of cyclohexanone, including the steps of feeding a crude reaction mixture to a first distillation column; and recovering a first side-cut fraction containing unreacted cyclohexanone from an intermediate tray of the first distillation column.

The present invention also provides, in another aspect, a process for producing ε-caprolactone by the oxidation of cyclohexanone, including the steps of feeding a crude reaction mixture to a first distillation column; distilling off a first distillate from the top of the first distillation column, the first distillate containing low boiling components including unreacted cyclohexanone; recovering a first side-cut fraction from an intermediate tray of the first distillation column, the first side-cut fraction containing unreacted cyclohexanone in a higher concentration than in the first distillate; recovering a first bottom liquid from the bottom of the first distillation column, the first bottom liquid containing high boiling components including ε-caprolactone; introducing the first side-cut fraction to a second distillation column; recovering a second bottom liquid containing unreacted cyclohexanone from the bottom of the second distillation column; recycling the second bottom liquid into the raw material cyclohexanone; introducing the first bottom liquid to a third distillation column to thereby yield a third distillate containing ε-caprolactone from the third distillation column.

According to the present invention, a side-cut fraction containing unreacted cyclohexanone in a high concentration is recovered from an intermediate tray other than the top and bottom of the first distillation column and is fed to the second distillation column. Therefore, the burden on the processing in the second distillation column can be mitigated, and high-quality ε-caprolactone can be economically produced in a high yield without changing reaction conditions.

In the production processes of the present invention, cyclohexanone may be oxidized using a peracid. The peracid is preferably an organic peracid and more preferable peracetic acid.

The crude reaction mixture may mainly contain the peracid, an acid derived from the peracid, a solvent for the peracid, cyclohexanone, ε-caprolactone, adipic acid, and a polymerized product of ε-caprolactone. The first side-cut fraction may mainly contain the peracid, an acid derived from the peracid, a solvent for the peracid, and cyclohexanone. The first distillate may mainly contain the peracid, an acid derived from the peracid, a solvent for the peracid, and cyclohexanone. The first bottom liquid may mainly contain ε-caprolactone, adipic acid, and a polymerized product of ε-caprolactone. The second bottom liquid may mainly contain an acid derived from the peracid and unreacted cyclohexanone. The third distillate may mainly contain ε-caprolactone.

Further objects, features and advantages of the present invention will become apparent from the following description of the preferred embodiments with reference to the attached drawings.

DESCRIPTION OF THE PREFERRED EMBODIMENTS

Figure 1:
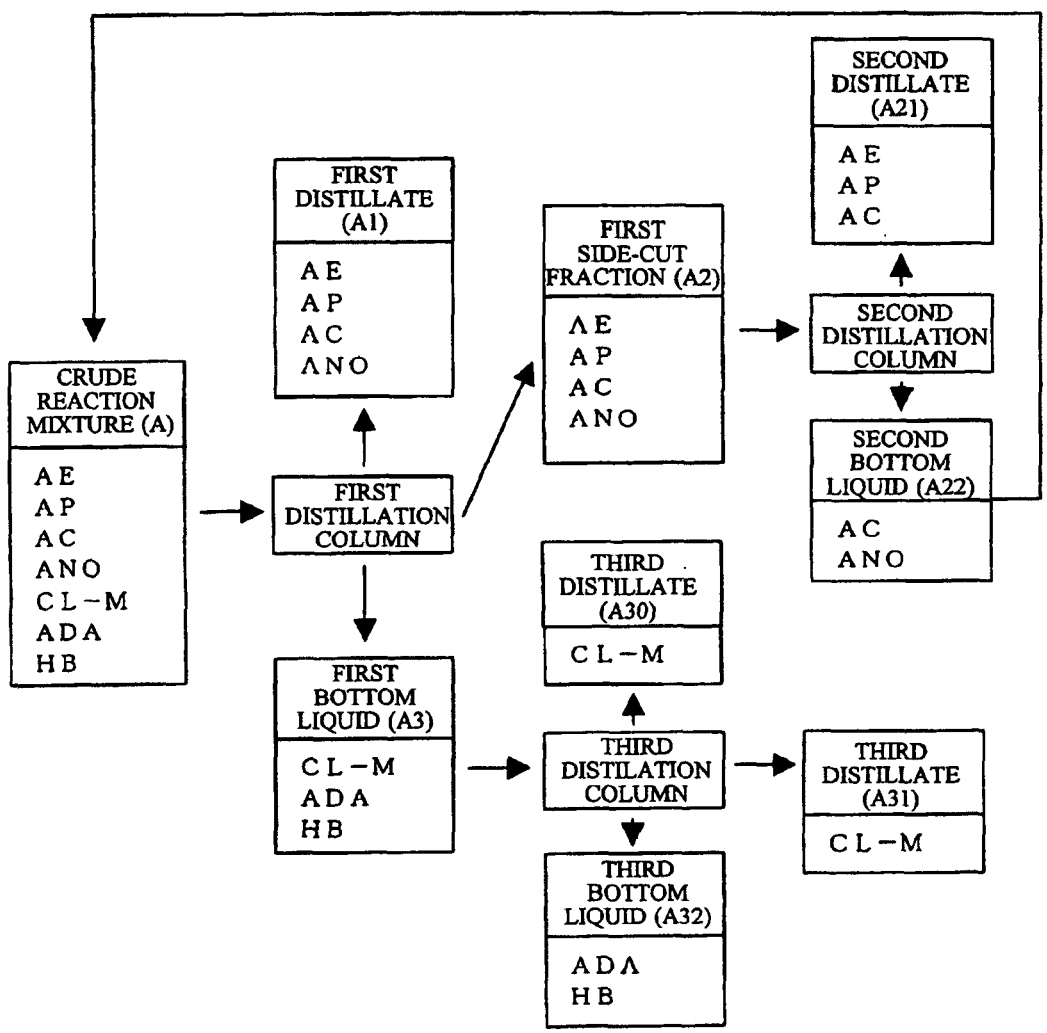
FIG. 1 is a schematic flow chart of a process for producing ε-caprolactone as an embodiment of the present invention.

FIG. 1 is a schematic flow chart of a process for producing ε-caprolactone as an embodiment of the present invention, in which abbreviations in frames represent main components of a distillate or bottom liquid.

Reaction

In this embodiment, ε-caprolactone is produced by the oxidation of cyclohexanone with a peracid. The peracid can be any of inorganic peracids and organic peracids, of which organic peracids are preferred. Such organic peracids include, for example, organic peroxoacids having —CO—OOH group, such as peroxyacetic acid (peracetic acid), peroxypropionic acid, and peroxyisobutyric acid, of which peracetic acid is typically preferred. The peracid is generally used in the form of a solution in a solvent such as acetone, ethyl acetate or acetic acid. For example, the organic peracid serves to oxidize cyclohexanone to yield ε-caprolactone and is generally converted into an acid having a boiling point lower than ε-caprolactone, such as acetic acid, propionic acid or isobutyric acid.

The above reaction yields a crude reaction mixture A containing ε-caprolactone (hereinafter briefly referred to as "CL-M") as a product, unreacted cyclohexanone (hereinafter briefly referred to as "ANO"), unreacted peracid (hereinafter briefly referred to as "AP"), a solvent for the peracid (hereinafter briefly referred to as "AE"), an acid corresponding to the peracid (hereinafter briefly referred to as "AC"), a polymerized product of ε-caprolactone (hereinafter briefly referred to as "HB") such as a caprolactone oligomer and/or caprolactone polymer, a by-product derived from cyclohexanone such as oxycaproic acid or adipic acid (hereinafter briefly referred to as "ADA"), and other by-products. From the crude reaction mixture A, individual components are separated and recovered according to the steps exemplified in FIG. 1.

In a co-oxidation process, ε-caprolactone is produced by the oxidation of cyclohexanone with air using acetaldehyde instead of the peracid, where necessary, in the presence of a catalyst. In this process, unreacted acetaldehyde corresponds to the unreacted peracid AP and acetic acid derived from acetaldehyde corresponds to the acid derived from the peracid AC in the process using the peracid.

First Distillation Column

According to the embodiment of FIG. 1, the crude reaction mixture A formed as a result of the above reaction is fed to a first distillation column. A first bottom liquid A3 mainly comprising high boiling components, ε-caprolactone CL-M, adipic acid ADA, and a polymerized product of ε-caprolactone HB, is recovered from the bottom of the first distillation column; a first distillate A1 mainly comprising low boiling components, unreacted cyclohexanone ANO, unreacted peracid AP, a solvent for the peracid AE, and an acid corresponding to the peracid AC, is recovered from the top, and a first side-cut fraction A2 mainly comprising low boiling components ANO, AP, AE, and AC is recovered from an intermediate tray other than the top and the bottom.

The distillation conditions in the first distillation column may be such that cyclohexanone can be recovered as a side-cut fraction from an intermediate tray of the distillation column and are preferably such that the concentration of cyclohexanone in the first side-cut fraction A2 is higher than that in the first distillate (first overhead) A1. They are more preferably such that the first distillate A1, the first side-cut fraction A2 and the first bottom liquid A3 have the compositions shown in FIG. 1, respectively. More specifically, in the first distillation column, the bottom temperature is, for example, from about 100° C. to about 200° C., and the column top pressure is, for example, lower than the normal atmospheric pressure and is preferably about 100 mmHg (13.3 kPa) or less. The distillation under reduced pressure can inhibit loss of ε-caprolactone due to polymerization in the crude reaction mixture A that contains multiple components and is thermally unstable with time.

The first side-cut fraction A2 can be recovered from any intermediate tray of the first distillation column, namely from any position other than the column top and bottom and is preferably recovered from a portion where the concentration of unreacted cyclohexanone is high, such as an intermediate tray between the column top and a tray from which the crude reaction mixture A is charged. The first side-cut fraction A2 can be extracted in any form of a liquid, a gas or a mixture thereof.

As a result of the above distillation procedure, substantially all of unreacted cyclohexanone contained in the crude reaction mixture A is distilled as the first distillate A1 and the first side-cut fraction A2. Even if the bottom liquid A3 contains unreacted cyclohexanone, the amount thereof is trivial. According to this embodiment, the first side-cut fraction A2 containing cyclohexanone in a higher concentration than in the first distillate A1 recovered from the column top is recovered and is fed to the second distillation column, thus mitigating the burden on the subsequent separation and purification procedure in the second distillation column.

The above-recovered first side-cut fraction A2 is introduced into the second distillation column to thereby recover unreacted cyclohexanone, and the first bottom liquid A3 is introduced into a third distillation column to thereby yield ε-caprolactone.

Second Distillation Column

In the embodiment shown in FIG. 1, the first side-cut fraction A2 recovered from the first distillation column is introduced into the second distillation column. A second distillate A21 mainly comprising low boiling components including the unreacted peracid AP, the solvent for the peracid AE, and the acid corresponding to the peracid AC is distilled off from the column top. A second bottom liquid A22 mainly comprising the unreacted cyclohexanone ANO and AC is recovered from the bottom and is then recycled into the raw material cyclohexanone.

The distillation conditions in the second distillation column may be such that cyclohexanone can be recovered from the bottom and are preferably such that the second distillate A21 and the second bottom liquid A22 have the compositions shown in FIG. 1. More specifically, in the second distillation column, the bottom temperature is, for example, from about 120° C. to about 200° C., and the column top pressure is, for example, about 50 mmHg (6.67 kPa) or less. The distillation under these conditions can prevent thermally unstable cyclohexanone contained in the first side-cut fraction A2 from deterioration.

The second bottom liquid A22 contains unreacted cyclohexanone in a high concentration and can be recycled, as intact, into the reaction system.

Third Distillation Column

According to the embodiment of FIG. 1, the first bottom liquid A3 recovered from the first distillation column is fed to the third distillation column. A third bottom liquid A32 containing high boiling components including adipic acid ADA and a polymerized product of ε-caprolactone HB is drained from the bottom of the third distillation column, and a third distillate A31 containing ε-caprolactone CL-M is recovered as a product.

The distillation conditions in the third distillation column may be such that ε-caprolactone can be recovered as a distillate (including a distillate from an intermediate tray) They are preferably such that the third distillate A31 and the third bottom liquid A32 have, for example, the compositions shown in FIG. 1. More specifically, in the third distillation column, the bottom temperature is, for example, from about 100° C. to about 200° C., and the column top pressure is, for example, about 50 mmHg (6.67 kPa) or less. For avoiding the polymerization of ε-caprolactone, the third distillate A31 is preferably recovered not from the column top but from an intermediate tray such as an intermediate tray between the column top and a tray from which the first bottom liquid A3 is charged. While not shown in FIG. 1, when ε-caprolactone is recovered from an intermediate tray, a third distillate A30 recovered from the column top may be introduced into the first distillation column for removing low boiling components. The third bottom liquid A32 contains multiple components such as ADA and HB, does not have a constant composition and is thereby generally disposed.

The present invention will be illustrated in further detail with reference to an example below, which is not intended to limit the scope of the invention. All percentages are by weight.

REFERENCE EXAMPLE 1

Into a flow reactor with a reaction inner capacity of 2 liters were fed cyclohexanone at 60 g/hr, a 30% solution of peracetic acid in ethyl acetate at 170.5 g/hr (at 51.4 g/hr in terms of pure peracetic acid, 1.1 times by mole that of cyclohexanone) for performing a continuous reaction at a reaction temperature of 50° C. The resulting crude reaction mixture was analyzed and was found to contain 28.78% of ε-caprolactone CL-M, 0.52% of unreacted cyclohexanone ANO, 1.31% of unreacted peracetic acid, 0.59% of by-produced adipic acid ADA, 0.30% of a polymerized product of caprolactone HB, 21.16% of acetic acid, 47.34% of ethyl acetate, and 0% of water.

EXAMPLE 1

According to the flow chart of FIG. 1, ε-caprolactone was produced. Initially, a crude reaction mixture A produced according to the procedure of Reference Example 1 was fed to a first distillation column and was subjected to distillation for removing low boiling components at a bottom temperature of 180° C. and a column top pressure of 90 mmHg (12.0 kPa). In the first distillation column, low boiling components including unreacted cyclohexanone ANO, unreacted peracetic acid, ethyl acetate and acetic acid were distilled as a first distillate A1 and a first side-cut fraction A2. The first side-cut fraction A2 contained ANO in a higher concentration than in the first overhead distillate A1. The first side-cut fraction A2 was introduced into a second distillation column, was subjected to distillation at a bottom temperature of 100° C. and a column top pressure of 225 mmHg (30.0 kPa) and thereby yielded a second distillate A21 containing unreacted peracetic acid, ethyl acetate, and acetic acid from the column top and a second bottom liquid A22 containing ANO and part of acetic acid from the bottom. The recovered second bottom liquid A22 was recycled as a reaction raw material to the reaction system. In the first distillation column, a first bottom liquid A3 containing the target ε-caprolactone CL-M, by-produced adipic acid ADA and a polymerization product of ε-caprolactone HB was recovered from the bottom. The recovered first bottom liquid A3 was introduced into a third distillation column and was subjected to distillation at a bottom temperature in a range from 120° C. to 200° C. and a column top pressure of 5 mmHg (0.67 kPa). In the third distillation column, the target ε-caprolactone was yielded as a third side-cut fraction A31 not from the column top but from an intermediate tray between the column top and a tray from which the first bottom liquid A3 was charged. A third bottom liquid A32 containing by-produced adipic acid ADA and a polymerized product of ε-caprolactone HB was drained from the bottom. Separately, a third overhead distillate A30 was recovered from the column top and was introduced into the first distillation column for removing low boiling components.

Quantitative operation conditions on charge, reflux, overhead distillation, side cut, and bottom liquid recovery in the first distillation column, those on reflux, distillation, and bottom liquid recovery (ANO recovery) in the second distillation column, and those on reflux, overhead distillation, side cut (product recovery) and bottom liquid drain in the third distillation column are shown in Tables 1—1, 1-2, and 1-3, respectively.

COMPARATIVE EXAMPLE 1

Figure 2:
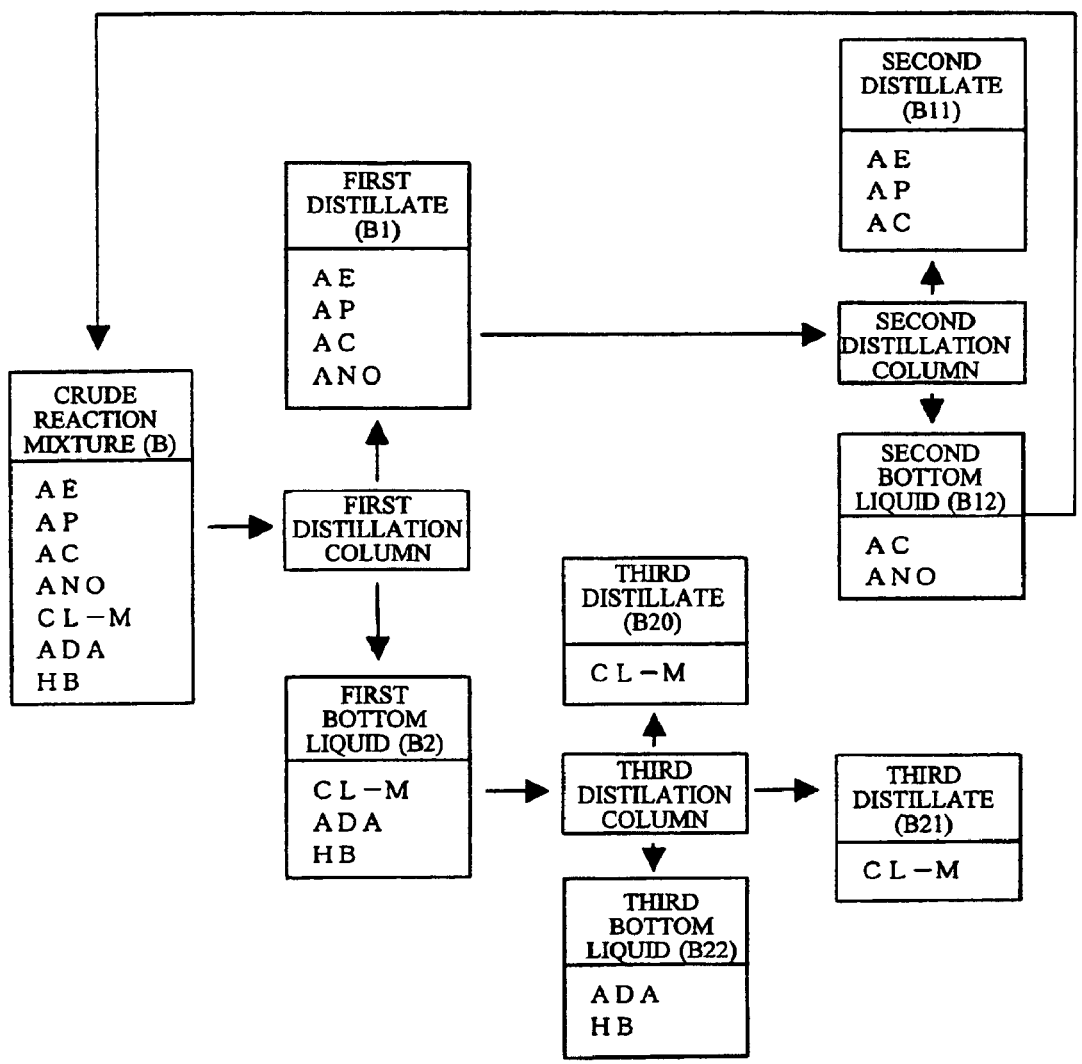
FIG. 2 is a schematic flow chart of a process for producing ε-caprolactone as Comparative Example 1.

According to the flow chart shown in FIG. 2, ε-caprolactone was produced. Initially, a crude reaction mixture B prepared according to the procedure of Reference Example 1 was fed to a first distillation column and was subjected to distillation for removing low boiling components at a bottom temperature of 200° C. and a column top pressure of 100 mmHg (13.3 kPa). In the first distillation column, low boiling components including unreacted cyclohexanone ANO, unreacted peracetic acid, ethyl acetate, and acetic acid was distilled as a first distillate B1. The first distillate B1 was introduced into a second distillation column and was subjected to distillation at a bottom temperature of 200° C. and a column top pressure of 100 mmHg (13.3 kPa). In this procedure, a second distillate B11 containing unreacted peracetic acid, ethyl acetate, and acetic acid was distilled off from the column top, and a second bottom liquid B12 containing unreacted cyclohexanone ANO and part of acetic acid was recovered from the bottom. A part of the second bottom liquid B12 was recycled as a reaction raw material to the reaction system, and the remainder was disposed. Separately, a first bottom liquid B2 containing the target product ε-caprolactone CL-M, by-produced adipic acid ADA, and a polymerized product of ε-caprolactone HB was recovered from the bottom of the first distillation column. The recovered first bottom liquid B2 was introduced into a third distillation column and was subjected to distillation at a bottom temperature in a range from 120° C. to 200° C. and a column top pressure of 50 mmHg (6.67 kPa). In this procedure, the target ε-caprolactone CL-M was recovered as a third distillate B21 not from the column top but from an intermediate tray between the column top and a tray from which the first bottom liquid B2 was charged, and a third bottom liquid B22 containing by-produced adipic acid ADA and a polymerized product of ε-caprolactone HB was drained from the bottom. A third overhead distillate B20 was recovered from the column top and was introduced into the first distillation column for removing low boiling components.

Quantitative operation conditions on charge, reflux, distillation, and bottom liquid recovery in the first distillation column, those on reflux, distillation, bottom liquid recovery (ANO recovery), and bottom liquid disposal (partial disposal) in the second distillation column, and those on reflux, overhead distillation, side cut (product recovery) and bottom liquid drain in the third distillation column are shown in Tables 2-1, 2—2, and 2-3, respectively.

In the tables below, the term "AP" means unreacted peracetic acid, the term "AE" means ethyl acetate, the term "AC" means acetic acid, and the term "LB" means other low-boiling components. And composition is referred to as the abbreviation "comp.".

TABLE 1-1

First Distillation Column (removal of low boiling components)

| Component | Charge Rate kg/hr | Charge Comp. wt. % | Reflux Rate kg/hr | Reflux Comp. wt. % | Overhead distillation Rate kg/hr | Overhead distillation Comp. wt. % | Side cut [to 2nd column] Rate kg/hr | Side cut [to 2nd column] Comp. wt. % | Bottom [to 3rd column] Rate kg/hr | Bottom [to 3rd column] Comp. wt. % |
|---|---|---|---|---|---|---|---|---|---|---|
| AE | 4449.9 | 45.5 | 4495.0 | 82.9 | 4086.3 | 82.9 | 363.6 | 18.2 | 0.0 | 0.0 |
| AC | 2249.4 | 23.0 | 879.2 | 16.2 | 799.3 | 16.2 | 1450.1 | 72.5 | 0.0 | 0.0 |
| AP | 117.4 | 1.2 | 47.1 | 0.9 | 42.8 | 0.9 | 74.6 | 3.7 | 0.0 | 0.0 |
| ANO | 78.2 | 0.8 | 1.74 | 0.0 | 1.6 | 0.0 | 76.6 | 3.8 | 0.0 | 0.0 |
| CL-M | 2840.0 | 29.0 | 0.0 | 0.0 | 0.0 | 0.0 | 35.1 | 1.8 | 2804.9 | 98.3 |
| $H_2O$ | 0.0 | 0.0 | 0.0 | 0.0 | 0.0 | 0.0 | 0.0 | 0.0 | 0.0 | 0.0 |
| LB | 0.0 | 0.0 | 0.0 | 0.0 | 0.0 | 0.0 | 0.0 | 0.0 | 0.0 | 0.0 |
| ADA | 48.9 | 0.5 | 0.0 | 0.0 | 0.0 | 0.0 | 0.0 | 0.0 | 48.9 | 1.7 |
| HB | 0.0 | 0.0 | 0.0 | 0.0 | 0.0 | 0.0 | 0.0 | 0.0 | 0.0 | 0.0 |
| Total | 9780.0 | 100 | 5423 | 100 | 4930.0 | 100 | 1999.9 | 100 | 2853.8 | 100 |

TABLE 1-2

Second Distillation Column (ANO recovery)

| Component | Reflux Rate kg/hr | Reflux Comp. wt. % | Distillation Rate kg/hr | Distillation Comp. wt. % | Bottom [ANO recovery] Rate kg/hr | Bottom [ANO recovery] Comp. wt. % |
|---|---|---|---|---|---|---|
| AE | 363.6 | 21.4 | 363.6 | 21.4 | 0.0 | 0.0 |
| AC | 1264.7 | 74.4 | 1264.7 | 74.4 | 185.5 | 61.8 |
| AP | 71.2 | 4.2 | 71.2 | 4.2 | 3.3 | 1.1 |
| ANO | 0.5 | 0.0 | 0.5 | 0.0 | 76.1 | 25.4 |
| CL-M | 0.0 | 0.0 | 0.0 | 0.0 | 35.1 | 11.7 |
| $H_2O$ | 0.0 | 0.0 | 0.0 | 0.0 | 0.0 | 0.0 |
| LB | 0.0 | 0.0 | 0.0 | 0.0 | 0.0 | 0.0 |
| ADA | 0.0 | 0.0 | 0.0 | 0.0 | 0.0 | 0.0 |
| HB | 0.0 | 0.0 | 0.0 | 0.0 | 0.0 | 0.0 |
| Total | 1700.0 | 100 | 1700.0 | 100 | 300.0 | 100 |

TABLE 1-3

Third Distillation Column (product recovery)

| Component | Reflux Rate kg/hr | Reflux Comp. wt. % | Overhead distillation [recycled for removing low boiling components] Rate kg/hr | Overhead distillation [recycled for removing low boiling components] Comp. wt. % | Bottom Rate kg/hr | Bottom Comp. wt. % | Side cut [product recovery] Rate kg/hr | Side cut [product recovery] Comp. wt. % |
|---|---|---|---|---|---|---|---|---|
| AE | 0.0 | 0.0 | 0.0 | 0.0 | 0.0 | 0.0 | 0.0 | 0.0 |
| AC | 0.0 | 0.0 | 0.0 | 0.0 | 0.0 | 0.0 | 0.0 | 0.0 |
| AP | 0.0 | 0.0 | 0.0 | 0.0 | 0.0 | 0.0 | 0.0 | 0.0 |
| ANO | 0.0 | 0.0 | 0.0 | 0.0 | 0.0 | 0.0 | 0.0 | 0.0 |
| CL-M | 3724.5 | 100 | 120.0 | 100 | 86.0 | 63.8 | 2718.9 | 100 |
| $H_2O$ | 0.0 | 0.0 | 0.0 | 0.0 | 0.0 | 0.0 | 0.0 | 0.0 |
| LB | 0.0 | 0.0 | 0.0 | 0.0 | 0.0 | 0.0 | 0.0 | 0.0 |
| ADA | 0.0 | 0.0 | 0.0 | 0.0 | 48.9 | 36.2 | 0.0 | 0.0 |
| HB | 0.0 | 0.0 | 0.0 | 0.0 | 0.0 | 0.0 | 0.0 | 0.0 |
| Total | 3724.5 | 100 | 120.0 | 100 | 134.9 | 100 | 2598.9 | 100 |

TABLE 2-1

First Distillation Column (removal of low boiling components)

| Component | Charge Rate kg/hr | Charge Comp. wt. % | Reflux Rate kg/hr | Reflux Comp. wt. % | Distillation [to 2$^{nd}$ column] Rate kg/hr | Distillation [to 2$^{nd}$ column] Comp. wt. % | Bottom [to 3$^{rd}$ column] Rate kg/hr | Bottom [to 3$^{rd}$ column] Comp. wt. % |
|---|---|---|---|---|---|---|---|---|
| AE | 4210.8 | 46.32 | 2105.4 | 65.51 | 4210.8 | 65.51 | 0.0 | 0.00 |
| AC | 1954.8 | 21.51 | 977.2 | 30.41 | 1954.3 | 30.41 | 0.5 | 0.02 |
| AP | 150.0 | 1.65 | 75.0 | 2.33 | 150.0 | 2.33 | 0.0 | 0.00 |
| ANO | 94.8 | 1.04 | 47.4 | 1.48 | 94.8 | 1.48 | 0.3 | 0.01 |
| CL-M | 2623.2 | 28.86 | 4.2 | 0.13 | 8.4 | 0.13 | 2725.9 | 97.95 |
| H$_2$O | 9.6 | 0.11 | 4.5 | 0.14 | 9.0 | 0.14 | 1.1 | 0.04 |
| LB | 0.1 | 0.00 | 0.1 | 0.00 | 0.1 | 0.00 | 0.0 | 0.00 |
| ADA | 27.6 | 0.30 | 0.0 | 0.00 | 0.0 | 0.00 | 27.6 | 0.99 |
| HB | 19.2 | 0.21 | 0.0 | 0.00 | 0.0 | 0.00 | 27.6 | 0.99 |
| Total | 9090.1 | 100 | 3213.7 | 100 | 6427.4 | 100 | 2783.0 | 100 |

TABLE 2-2

Second Distillation Column (ANO recovery)

| Component | Reflux Rate kg/hr | Reflux Comp. wt. % | Distillation Rate kg/hr | Distillation Comp. wt. % | Bottom [ANO recovery] Rate kg/hr | Bottom [ANO recovery] Comp. wt. % | Bottom [partial disposal] Rate kg/hr | Bottom [partial disposal] Comp. wt. % |
|---|---|---|---|---|---|---|---|---|
| AE | 1263.2 | 67.65 | 4210.8 | 67.65 | 0.0 | 0.00 | 0.0 | 0.00 |
| AC | 556.3 | 29.79 | 1854.3 | 29.79 | 80.0 | 49.23 | 20.0 | 49.14 |
| AP | 45.0 | 2.41 | 150.0 | 2.41 | 0.0 | 0.00 | 0.0 | 0.00 |
| ANO | 0.0 | 0.00 | 0.0 | 0.00 | 75.8 | 46.65 | 19.0 | 46.68 |
| CL-M | 0.0 | 0.00 | 0.0 | 0.00 | 6.7 | 4.12 | 1.7 | 4.18 |
| H$_2$O | 2.7 | 0.15 | 9.0 | 0.15 | 0.0 | 0.00 | 0.0 | 0.00 |
| LB | 0.0 | 0.00 | 0.1 | 0.00 | 0.0 | 0.00 | 0.0 | 0.00 |
| ADA | 0.0 | 0.00 | 0.0 | 0.00 | 0.0 | 0.00 | 0.0 | 0.00 |
| HB | 0.0 | 0.00 | 0.0 | 0.00 | 0.0 | 0.00 | 0.0 | 0.00 |
| Total | 1867.2 | 100 | 6224.2 | 100 | 162.5 | 100 | 40.7 | 100 |

TABLE 2-3

Third Distillation Column (product recovery)

| Component | Reflux Rate kg/hr | Reflux Comp. wt. % | Overhead distillation [recycled for removing low boiling components] Rate kg/hr | Overhead distillation [recycled for removing low boiling components] Comp. wt. % | Bottom Rate kg/hr | Bottom Comp. wt. % | Side cut [product recovery] Rate kg/hr | Side cut [product recovery] Comp. wt. % |
|---|---|---|---|---|---|---|---|---|
| AE | 0.0 | 0.00 | 0.0 | 0.00 | 0.0 | 0.00 | 0.0 | 0.00 |
| AC | 0.0 | 0.00 | 0.0 | 0.00 | 0.0 | 0.00 | 0.5 | 0.02 |
| AP | 0.0 | 0.00 | 0.0 | 0.00 | 0.0 | 0.00 | 0.0 | 0.00 |
| ANO | 0.0 | 0.00 | 0.3 | 0.25 | 0.0 | 0.00 | 0.0 | 0.00 |
| CL-M | 3602.4 | 99.54 | 119.5 | 99.33 | 33.0 | 23.88 | 2523.4 | 99.96 |
| H$_2$O | 15.6 | 0.43 | 0.5 | 0.42 | 0.0 | 0.00 | 0.6 | 0.02 |
| LB | 1.2 | 0.03 | 0.0 | 0.00 | 0.0 | 0.00 | 0.0 | 0.00 |
| ADA | 0.0 | 0.00 | 0.0 | 0.00 | 27.1 | 19.61 | 0.0 | 0.00 |
| HB | 0.0 | 0.00 | 0.0 | 0.00 | 78.1 | 56.51 | 0.0 | 0.00 |
| Total | 3619.2 | 100 | 120.3 | 100 | 138.2 | 100 | 2524.5 | 100 |

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing ε-caprolactone by the oxidation of cyclohexanone, comprising the steps of:

feeding a crude reaction mixture to a first distillation column having a column bottom temperature from about 100° C. to about 200° C. and a column top pressure of about 100 mmHg or less;

distilling off a first distillate from the top of the first distillation column, the first distillate containing low boiling components including unreacted cyclohexanone;

recovering a first side-cut fraction from an intermediate tray of the first distillation column, the first side-cut fraction containing unreacted cyclohexanone in a higher concentration than in the first distillate;

recovering a first bottom liquid from the bottom of the first distillation column, the first bottom liquid containing high boiling components including ε-caprolactone;

introducing the first side-cut fraction to a second distillation column;

recovering a second bottom liquid containing unreacted cyclohexanone from the bottom of the second distillation column;

recycling the second bottom liquid into the raw material cyclohexanone;

introducing the first bottom liquid to a third distillation column to thereby yield a third distillate containing ε-caprolactone from the third distillation column.

2. The process according to claim 1, further comprising oxidizing cyclohexanone with a peracid.

3. The process according to claim 2, wherein the peracid is an organic peracid.

4. The process according to claim 3, wherein the organic peracid is peracetic acid.

5. The process according to claim 2, wherein the crude reaction mixture mainly comprises the peracid, an acid derived from the peracid, a solvent for the peracid, cyclohexanone, ε-caprolactone, adipic acid, and a polymerized product of ε-caprolactone.

6. The process according to claim 2, wherein the first side-cut fraction mainly comprises the peracid, an acid derived from the peracid, a solvent for the peracid, and cyclohexanone.

7. The process according to claim 2, wherein the first distillate mainly comprises the peracid, an acid derived from the peracid, a solvent for the peracid, and cyclohexanone.

8. The process according to claim 2, wherein the first bottom liquid mainly comprises ε-caprolactone, adipic acid, and a polymerized product of ε-caprolactone.

9. The process according to claim 2, wherein the second bottom liquid mainly comprises an acid derived from the peracid and unreacted cyclohexanone.

10. The process according to claim 2, wherein the third distillate mainly comprises ε-caprolactone.

* * * * *